United States Patent
Clark

(10) Patent No.: US 8,131,355 B2
(45) Date of Patent: Mar. 6, 2012

(54) AUTOMATED SKIN ELECTRICAL RESISTANCE MEASUREMENT DEVICE AND METHOD

(76) Inventor: James Hoyt Clark, Orem, UT (US)

( * ) Notice: Subject to any disclaimer, the term of this patent is extended or adjusted under 35 U.S.C. 154(b) by 711 days.

(21) Appl. No.: 11/888,390

(22) Filed: Aug. 1, 2007

(65) Prior Publication Data

US 2009/0036793 A1   Feb. 5, 2009

(51) Int. Cl.
*A61B 5/05* (2006.01)

(52) U.S. Cl. ...................................... 600/547

(58) Field of Classification Search ................... 600/547, 600/306, 372, 382, 384, 386, 390, 546, 548, 600/554, 587, 595
See application file for complete search history.

(56) References Cited

U.S. PATENT DOCUMENTS

| | | | |
|---|---|---|---|
| 5,421,344 A | 6/1995 | Popp | |
| 5,626,617 A | 5/1997 | Brewitt | |
| 6,024,734 A | 2/2000 | Brewitt | |
| 6,167,299 A | 12/2000 | Galchenkov et al. | |
| 6,485,480 B1 | 11/2002 | Brewitt | |
| 6,762,609 B2 | 7/2004 | Alanen et al. | |
| 7,052,472 B1 | 5/2006 | Miller et al. | |
| 2004/0087838 A1* | 5/2004 | Galloway et al. | 600/300 |
| 2004/0204658 A1 | 10/2004 | Dietz et al. | 600/547 |
| 2007/0066874 A1 | 3/2007 | Cook | 600/300 |

OTHER PUBLICATIONS

H. Leonhardt, M.D., and Hartwig Schuldt, M.D.M.SC., "An Introduction to Eletro-Acupuncture According to Voll", Magazine, 1976, 20 Pages, West Germany.
Reinhold Voll, M.D. and Richard Wagner-Strasse, "The Phenomenon of Medicine Testing in Electroacupuncture According to Voll", Magazine, Apr.-Jun. 1980, 11 Pages, West Germany.
Energetic-Medicine, "The Bionetics Phazx BodyCScan 2010-Biofeedback Acupuncture", Internet Advertisement, Jul. 10, 2006, Unknown Location.
Zyto, "How the LSA System Works", Internet Article, 2006, 4 Pages, Orem, Utah.
Maria Reichmanis, Andrew A. Marino and Robert O. Becker, "Electrical Correlates of Acupuncture Points", Magazine (IEEE Transactions on Biomedical Engineering), Nov. 1975, 3 Pages, Unknown Location.
Title: A Guide to Tyodoraku Therapy; Author: Oriental Medicine and the Pain Clinic, The Department of Anesthesiology; Date: Prior to Jul. 11, 2006; Pertinent Pages: p. 1 of 8 through 8 of 8.
Title: The Digital Health Clinic of Complimentary Medicine; Author: Digital Health Clinic of Complimentary Medicine; Date: Prior to Jul. 10, 2006; Pertinent pp. 1 through 6 (unnumbered pages).

* cited by examiner

*Primary Examiner* — Jeffrey G Hoekstra
(74) *Attorney, Agent, or Firm* — J. David Nelson

(57) ABSTRACT

An automated skin resistance measurement device having an applied signal selector for selecting one or more applied signal forms from an applied signal library, an applied signal generator in communication with the applied signal selector for generating one or more DC applied signals, each applied signal being in the form of a selected applied signal form, one or more applied signal applicators for administering the applied signals to test zones on the skin of a human subject, and one or more applied signal resistance sensors for sensing the resistance of the skin of the subject at the test zones.

45 Claims, 2 Drawing Sheets

AUTOMATED SKIN ELECTRICAL RESISTANCE MEASUREMENT DEVICE AND METHOD

FIELD OF THE INVENTION

This invention is in the field of electrical resistance measuring devices and methods and in particular the field of devices and methods for measuring the electrical resistance of an area of the skin of a human subject.

BACKGROUND OF THE INVENTION

A procedure for taking resistance readings on the skin was formalized by Dr. Reinhold Voll, M.D., in the 1950's. Voll developed the Dermatron, a solid-state, non-computerized device with a single ohmmeter that measured with a direct current (DC). The Dermatron was calibrated to read DC resistance from about 1 million ohms to 0 ohm. Voll set the scale on the Dermatron to read from 0 (for 1 million ohms) to 100 (for 0 ohm). Today this scale is given in units called volls.

Voll called his procedure Electroacupuncture According to Voll or EAV. He measured resistance at the location of classical Chinese acupuncture points and at locations that he and other medical doctors discovered. Voll called each location a measurement point or MP.

When Voll used the Dermatron, the patient held a metal ground cylinder in one hand, while Voll touched a measurement point (MP) on the other hand with a stylus type probe. After touching the MP, Voll observed the resistance reading rise to a maximum. After the reading reached the maximum, Voll continued to hold the probe on the skin, and he watched for a drop in the reading. As long the reading dropped, Voll kept the probe contacting the skin. When the reading remained level for a few seconds, Voll would stop the reading by lifting the probe from the skin. He would then manually record the maximum value and the difference between the maximum value and the lowest value after the drop. He called the difference the indicator drop or ID. The time for the ID was variable and the time was not recorded.

Today EAV is often called Electro Dermal Screening or EDS, because the name Electroacupuncture According to Voll has been confused with the process of attaching electrodes to acupuncture needles that are inserted into the skin, a process also called electroacupuncture.

Subsequent studies have established the scientific basis for EAV/EDS. An IEEE publication shows the use of an ohmmeter to measure acupuncture points. Further, the study presents the electrical properties of the skin and particularly at the acupuncture points.

Another device for measuring energy at acupuncture points was developed by Yosio Nakatani in 1950, which he called Ryodoraku. An operator manually measured with a single ohmmeter on the Ryodoraku device in a manner similar to the procedure used with the Dermatron.

U.S. Pat. No. 5,421,344 to Popp discloses an apparatus in the form of a single probe with multiple needle-like sensors to measure a single acupuncture point. Further, Popp disclosed a method for using a computer to analyze the statistical distribution of the readings and compare the statistical distribution of the readings.

U.S. Pat. No. 6,762,609 to Alanen discloses a device which measures, through the use of a probe, skin surface hydration as a capacitance value.

U.S. Pat. No. 7,052,472 to Miller discloses a device which measures the level of skin perspiration using a conductance sensing system for detecting symptoms of hypoglycemia.

In 1980, the present inventor developed a computerized EDS device. Because his technology was the first computerized EDS device, he called it Computerized EDS or CEDS.

The measurement apparatus for CEDS, like EAV/EDS or Ryodoraku, is a single ohmmeter operated by a person, but the measurement data is analyzed, stored, displayed and printed using a digital computer in communication with the ohmmeter. The method for CEDS uses computer algorithms to analyze the resistance measurements to determine a dynamic set of values B Maximum Resistance (Max), Minimum Resistance (Min), the rate of increase (Ris) of resistance to the Maximum Resistance, and the rate of decrease (Fal) from the Maximum Resistance to the Minimum Resistance. The Max, Min, Ris, and Fal are computed after the reading is taken by the operator. Max is the highest resistance reading value obtained after the operator touches the acupuncture point or other MP. The Ris is the average slope of the resistance curve from the time the operator touches the MP and the time the maximum resistance is reached, i.e. the increase in resistance divided by the time elapsed to reach the maximum resistance. The maximum resistance point is ascertained so the operator may then observe for any drop in the reading as Voll established for EAV/EDS. The Min is a lower steady state resistance value reached after the drop in the resistance reading after the Max is reached. The Fal is the average negative slope of the resistance curve from the time the maximum is reached and the time the Min is reached, i.e. the decrease in the resistance from the Max to the Min divided by the time elapsed between the Max occurrence and the Min occurrence.

Voll mentions the rate of increase of the resistance as an important way to locate an MP. However he taught that the ID presented the most useful information for the MP's condition. For preferred embodiments of the present invention, the ID is not used.

In U.S. Pat. No. 5,626,617 to Brewitt, the inventor discloses that the Max, Min, Ris and Fal values from each reading are analyzed. The inventor discloses that she uses the CEDS device, also referred to as the LISTEN device, which was developed by the present inventor, for making the measurements.

For CEDS, Clark also developed a signal generator and a database of signals that simulated homeopathic and other products when the signals were output. The operator selected products to be output and controlled when a signal was turned ON or OFF. The present-day Dermatron is computerized as are many other EAV/EDS devices from other manufacturers. All the known devices use a single DC ohmmeter under manual control.

Some computerized EAV/EDS type devices have been marketed under the names such as Eclosion, Phazx BodyScan, QXCI, and SCIO. The manufacturers have asserted that their respective devices measure signals using bands placed around the head and the wrists without the need of an operator. The developers for each of these devices state that they measure the body's resonance/reactance pattern. The Phazx website (phazx.com) states that BodyScan and QXCI are based on EAV and that BodyScan records voltage, frequency and current measurements. The devices apparently require a human operator making the measurements using a single EAV/EDS probe.

The Limbic Stress Assessment (LSA) System from Vaughan R. Cook, OMD at The Digital Health Clinic, which apparently is also associated with Zyto, has a touch plate with multiple positions to place the fingers. The LSA System supposedly records and analyzes subconscious responses. The developer for this device claims that it is used to create a personalized "Stress Profile" of the subject that guides the practitioner in making decisions for remedies and/or therapies. The LSA website (zyto.com) apparently discloses a galvanic skin resistance measuring device (GSR), which is the type of apparatus used by other EAV/EDS devices.

An objective of the present invention is to provide an apparatus and method for the selective, automated administration of one or more applied signals to one or more test zones on the skin of a subject for the completion of skin resistance measurements for each test zone. A test zone may be an MP as defined above or may be the area of the skin of the subject in contact with a contact pad or other signal applicator.

A further objective of the present invention is to provide an apparatus and method for the selective, automated administration of one or more applied signals, the applied signals comprising one or more applied signal segments which may be of positive or negative voltage, to one or more test zones on the skin of a subject for the completion of skin resistance measurements for each test zone.

A still further objective of the present invention is to provide an apparatus and method for the selective, automated administration of one or more applied signals, the applied signals being a composite of one or more base signals of a selected constant voltage, positive or negative, and a stimulus signal with variable voltage segments which may be of positive or negative voltage, to one or more test zones on the skin of a subject for the completion of skin resistance measurements for each test zone.

A still further objective of the present invention is to provide an apparatus and method for the selective, automated, and coordinated administration of one or more applied signals to one or more test zones on the skin of a subject for the completion of skin resistance measurements for each test zone.

A still further objective of the present invention is to provide an apparatus and method for the selective, automated, and coordinated administration of one or more applied signals to one or more test zones on the skin of a subject for the determination, for each test zone, of a skin resistance time function, i.e. skin resistance as a function of time, for a selected time period.

A still further objective of the present invention is to provide an apparatus and method for the selective, automated, and coordinated administration of one or more applied signals to one or more test zones on the skin of a subject for the determination, for each test zone, of a skin resistance time function, i.e. skin resistance as a function of time, for a selected time period and the extraction of other resistance functions or factors, such as maximum resistance and rate of change of resistance from the time of applied signal initiation to the time of maximum resistance.

A still further objective of the present invention is to provide an apparatus and method for the selective, automated, and coordinated administration of one or more applied signals to one or more test zones on the skin of a subject for the determination, for each test zone, of a skin resistance time function, i.e. skin resistance as a function of time, for a selected time period, and the extraction of a resistance vector having the change in resistance as one vector component and the corresponding elapsed time as another vector component.

SUMMARY OF THE INVENTION

The electrical resistance posed by any potential path for the passage of current is determined by measuring the amount of electrical current that will pass along the path for a given applied electromotive force (voltage). The relationship of resistance (R), voltage (V), and current (I) is expressed by the equation $V=IR$. Rewritten, the resistance exhibited by the path is expressed by the equation $R=V/I$. In other words, for a known applied voltage, the resistance is equal to the applied voltage divided by the current that flows along the path as a result of the applied voltage. For many substances, resistance is not generally constant as the applied voltage varies, and thus the resulting current will not necessarily vary proportionally. Furthermore, even when a constant voltage is applied to a path, the resulting current will often vary with time. That is particularly the case when a voltage is applied to the skin of a human being. Typically the resultant current will increase rapidly and then the resistance of the skin will increase, causing a decrease in the current. The resistance typically will reach a maximum and then will decrease somewhat to a more or less steady state resistance value, the resistance and the resultant current then remaining fairly constant. The time period for reaching the steady state values will vary somewhat, but it is typically ranges between a fraction of a second and a few seconds.

DETAILED DESCRIPTION

Figure 1:
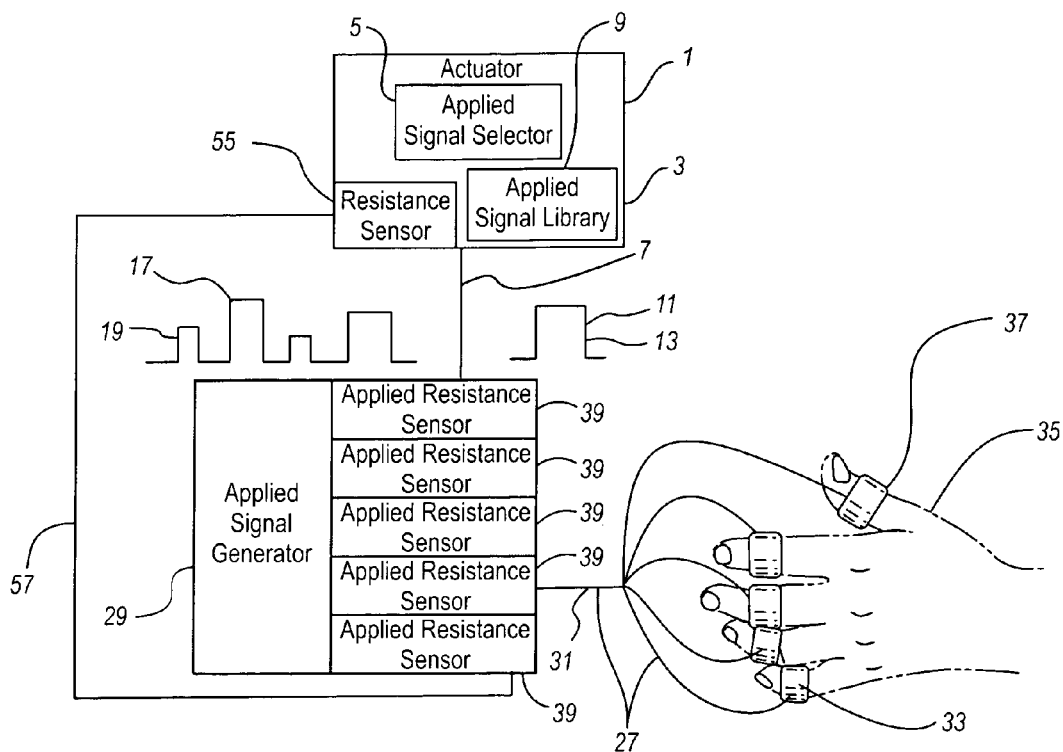
FIG. 1 is a schematic illustration of a preferred embodiment of the automated skin electrical resistance measuring device of the present invention.
Figure 2:
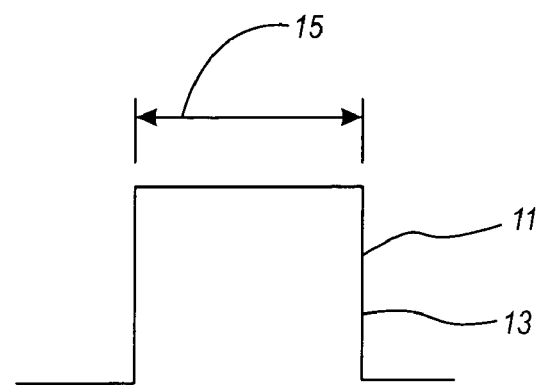
FIG. 2 is an illustration of a constant voltage square wave signal of a base signal of a preferred embodiment of an applied signal form of the present invention.
Figure 3:
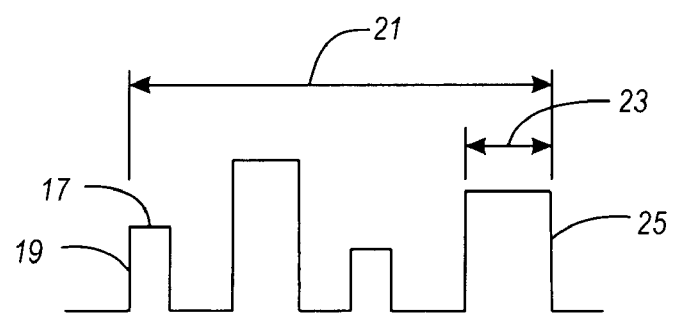
FIG. 3 is an illustration of a variable voltage square wave signal of a stimulus signal of a preferred embodiment of an applied signal form of the present invention.

Referring first to FIG. 1, a block diagram schematic of a preferred embodiment of the automated skin electrical resistance measuring device 1 of the present invention is shown. An actuator 3, which, based upon current technology, may incorporate a digital circuit with a keyboard or other input devices known to persons skilled in the art, includes an applied signal selector 5 which is used by the operator to select an applied signal form 7 from an applied signal library 9 stored in the actuator. Referring also to FIG. 2 and FIG. 3, the applied signal form 7 may consist of a base signal 11 which may be a constant voltage square wave signal 13 having a base signal time period 15, a stimulus signal 17 which may consist of a variable voltage square wave signal 19 having an overall stimulus signal time period 21 and a variable stimulus segment time period 23 for a respective stimulus signal segment 25, or a compound stimulus signal which may consist of a combination of two or more stimulus signals. Further, the applied signal may consist of a composite of a base signal and a stimulus signal or a composite of a base signal and a compound stimulus signal.

Although the base signal 11 is illustrated in FIG. 1 and FIG. 2 with a positive voltage, and the stimulus signal 17 is shown in FIG. 1 and FIG. 3 with positive voltage segments, the voltage of a base signal, a stimulus signal or any stimulus signal segment may be positive or negative. The actuator may provide the operator with the option of reversing the polarity of any base signal or any stimulus signal or alternatively may provide a library of base signals or stimulus signals with the polarity reversed.

Referring again to FIG. 1, as stated above, the actuator 3 includes an applied signal selector 5 which is used by the operator to select an applied signal form 7. The actuator transmits the selected applied signal form 7 from the applied signal selector to the applied signal generator 29, which may also be incorporated in the actuator. The applied signal generator generates an applied signal 31 based upon the selected applied signal form. If the applied signal generator is directly connected by applied signal conductors 27 in wire form to the applied signal applicators 33 as shown in FIG. 1, the applied signals as generated by the applied signal generator 29 may be in the form of DC voltage signals in the form of the applied signal form 7. The selected applied signal form may be transmitted by wireless communication to the applied signal generator, if it is desirable to electrically or physically separate the actuator and the applied signal generator.

Furthermore, a single actuator may be used to actuate multiple applied signal generators. For example, a single actuator may be used to transmit applied signals to multiple applied signal generators which are each connected to one or more subjects in a clinical setting. For those embodiments, the actuator may include a transmitter which may be selected from a number of types which are known in the art. Each applied signal generator may then have a receiver which is compatible with the transmitter. Each applied signal generator may generate an applied signal 31, which for the preferred embodiment shown is a DC voltage signal, and the applied signal generator may be directly coupled by respective applied signal conductors 27 to each of the applied signal applicators 33 which are affixed to the subject 35, thereby administering the applied signal to one or more test zones 37 of the subject.

As an applied signal is applied to a test zone, the voltage of the applied signal causes an electric current to flow through a path in the skin of the subject, the path being determined primarily by the type and design of the applied signal applicator and the characteristics of the skin of the subject. As indicated above, the instantaneous resistance (R) is defined at each moment as the applied voltage (V) divided by the resultant current (I). R will vary with time as V is applied, which is demonstrated by the variation with time of the resultant current. The resistance of each test zone 37 on the skin of the subject may be continuously monitored by a respective applied signal resistance sensor 39. These sensors may be ohmmeters integral with the applied signal applicators which simultaneously measure current and voltage or may be current meters with the resistance calculated based upon the measured current and the known voltage of the applied signal. Resistance data 57 may be continuously transmitted from each of the sensors to a resistance memory which may be incorporated in the actuator. Various display, printing, and other output devices known in the art may be incorporated into or connected peripherally with the actuator to visually, audibly or electronically output the resistance data.

Figure 4:
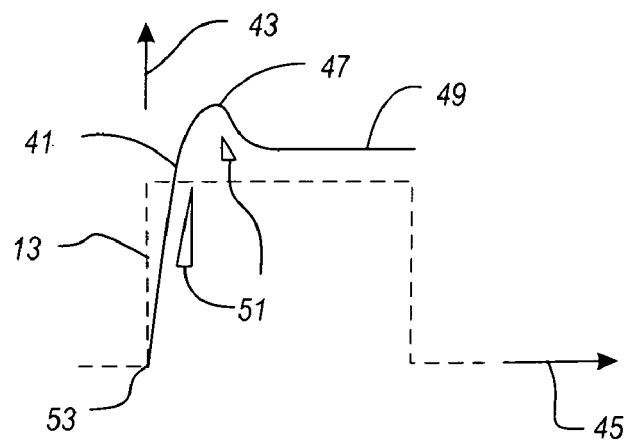
FIG. 4 is an illustration of a typical resistance curve showing resistance varying as a function of time with the application of a constant voltage square wave applied signal of the present invention.

Referring to FIG. 4, a typical resistance curve 41 showing R 43 varying as a function of time (t) 45 with the application of an applied signal 31 having the form of a constant voltage square wave applied signal 13 is shown. The resistance will typically increase until it reaches a maximum resistance 47 and then it will decrease to a post maximum, minimum resistance 49, and the resistance will generally stabilize at that level so long as the applied voltage remains constant. The rate at which the resistance increases to the maximum resistance is the resistance time function slope 51 at any time between signal initiation 53 and maximum resistance 47. Likewise the resistance time function slope defines the rate, at any time between maximum resistance and post-maximum minimum resistance 49, at which the resistance decreases from the maximum resistance to the post-maximum minimum resistance.

Maximum resistance, minimum resistance, slope of the resistance time function before maximum resistance, slope of the resistance time function after maximum resistance, and other information contained in the resistance time function, for a given applied signal, are useful variables or factors, herein referred to collectively as resistance functions, for use with the devices described in the Background of the Invention presented above.

Figure 5:
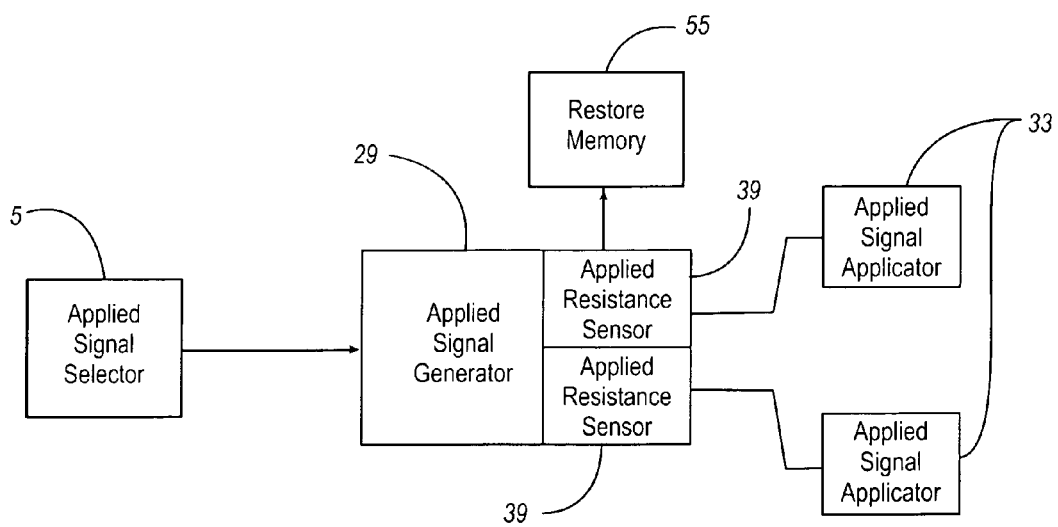
FIG. 5 is a schematic illustration of a simplified embodiment of the present invention.

Simplified embodiments of the present invention as shown in FIG. 5 may comprise an applied signal selector 5, an applied signal generator 29 in communication with the applied signal selector, one or more applied signal applicators 33 in communication with the applied signal generator, and one or more applied signal resistance sensors 39. The simplest embodiments may provide for the direct coupling of the applied signal selector and the applied signal generator, and for the direct coupling of the applied signal generator and the applied signal applicators. The applied signal applicators may each also be direct coupled with applied signal resistance sensors, which may be ohmmeters or current meters, which would continuously monitor the resistance or monitor the current from the applied signal applicator, thereby providing for the computation of resistance based upon the known voltage.

Resistance values as measured for a selected time period are stored in resistance memory 55 or transmitted to a peripheral storage device, providing for the determination of a resistance time function for the selected time period. For the simplified embodiments, an actuator may comprise the applied signal-selector, the applied signal generator, and the resistance memory.

Sophisticated embodiments of the present invention may provide for selection by the operator of a plurality of unique applied signals, thereby providing for a unique applied signal being provided to each of a plurality of applied signal applicators. The operator may select operation options, thereby providing for the respective applied signals to be applied through the respective signal applicators to the respective test zones simultaneously, consecutively, or in any sequence desired. The operator may select a base signal which is a square wave of constant voltage, a variable voltage stimulus signal, a compound signal, or a composite signal. The operator may select sequential applied signals to be applied according to timing selected by the operator. Thus the operator may affix multiple applied signal applicators to various test zones on the subject, apply uniform or unique applied signals during simultaneous or sequential time periods to the test zones, and measure and record the resistance of each of the test zones for any selected time period. The actuator may incorporate the applied signal selector, the applied signal generator, and resistance function storage. The actuator may provide the communication link between the applied signal selector, the applied signals generator, the applied signal applicators, and the applied signal resistance sensors. The actuator may be a digital computer with a keyboard or other input means used by the operator to make the selections. A specially designed keyboard, keypad or other control panel may simplify the operation.

Other embodiments and other variations and modifications of the embodiments described above will be obvious to a person skilled in the art. Therefore, the foregoing is intended to be merely illustrative of the invention and the invention is limited only by the following claims and the doctrine of equivalents.

What is claimed is:

1. Apparatus for the automated measurement of a resistance time function which is resistance as a function of time for a selected time interval for one or more test zones on the skin of a human subject, the apparatus comprising:
   applied signal selector;
   applied signal generator in communication with the applied signal selector for generating one or more applied signals;
   one or more applied signal applicators in communication with the applied signal generator, each applied signal applicator being attachable to one of the test zones and having a capability for automated, continuous application, for a selected signal application time interval, of the one or more applied signals generated by the applied signal generator;
   one or more applied signal resistance sensors, each applied signal resistance sensor being attachable to one of the test zones and having a capability for automated, continuous measurement of resistance for a selected resistance measurement time interval;
   resistance memory in communication with the applied signal resistance sensors; and
   an actuator in communication with the resistance memory, the actuator having a capability for the determination of resistance as a function of time, the resistance time function.

2. Apparatus as recited in claim 1 wherein the applied signal selector further comprises an applied signal memory and an applied signal library stored on the applied signal memory.

3. Apparatus as recited in claim 1 wherein the applied signal selector further comprises an applied signal memory and an applied signal library stored on the applied signal memory.

4. Apparatus as recited in claim 1 wherein one or more of the applied signal applicators is an electrical contact connection or pad.

5. Apparatus as recited in claim 1 wherein one or more of the applied signal applicators is an electrical contact finger connection or pad.

6. Apparatus as recited in claim 5 wherein each of the electrical contact finger connections or pads has a finger band for fixedly positioning the electrical contact finger connection or pad against a desired test zone on a selected finger of the human subject.

7. Apparatus as recited in claim 1 wherein each signal resistance sensor is an ohmmeter.

8. Apparatus as recited in claim 1 wherein the voltage characteristics of the applied signal is known and wherein each signal resistance sensor is a current meter which measures the current flowing from a respective applied signal applicator to a respective test zone.

9. Apparatus as recited in claim 1 wherein a maximum resistance measured during a selected time interval is determined from the resistance time function.

10. Apparatus as recited in claim 9 wherein a minimum resistance measured following the maximum resistance during the selected time interval is determined from the resistance time function.

11. Apparatus as recited in claim 10 wherein a resistance fall rate, which is the resistance decrease between the maximum resistance and the minimum resistance, divided by an elapsed fall time between the time of the maximum resistance and the time of the minimum resistance is determined from the resistance time function.

12. Apparatus as recited in claim 9 wherein a resistance rise rate which is the maximum resistance divided by an elapsed rise time between the time of the maximum resistance and the time the applied signal is applied to the respective test zone is determined from the resistance time function.

13. Apparatus as recited in claim 1 wherein a resistance vector is determined from the resistance time function.

14. Apparatus as recited in claim 1 wherein a slope of the resistance time function as a function of time is determined from the resistance time function.

15. Apparatus as recited in claim 1 wherein a resistance vector having a maximum resistance measured during a selected time interval as one vector component and an elapsed rise time between the time of the maximum resistance and the time the applied signal is applied to the respective test zone as another vector component is determined from the resistance time function.

16. Apparatus as recited in claim 1 wherein the actuator is in communication with the applied signal selector, the applied signal generator, the applied signal applicator, and the applied signal resistance sensors.

17. Apparatus as recited in claim 1 wherein the actuator is a digital computer.

18. Apparatus as recited in claim 1 further comprising a digital computer actuator, the actuator having applied signal memory and an applied signal library stored on the applied signal memory.

19. Apparatus as recited in claim 1 further comprising a digital computer actuator, the actuator having resistance memory in communication with the applied signal resistance sensors.

20. Apparatus as recited in claim 1 wherein the applied signal is a base signal comprising a constant voltage square wave signal applied for a base signal time period.

21. Apparatus as recited in claim 1 wherein the applied signal is a stimulus signal comprising a variable square wave signal applied for a stimulus signal time period.

22. Apparatus as recited in claim 1 wherein the applied signal is a composite signal comprising a base signal which comprises a constant voltage square wave signal applied for a base signal time period and a stimulus signal which comprises a variable square wave signal applied for a stimulus signal time period.

23. Apparatus for the automated measurement of a resistance time function which is resistance as a function of time for a selected time interval for one or more test zones on the skin of a human subject, the apparatus comprising:
   applied signal selector for use by a user in selecting one or more applied signal forms;
   applied signal generator in communication with the applied signal selector for generating a respective applied signal for each selected applied signal form, each applied signal being an electric voltage signal in the form of the applied signal form for which it is generated;
   one or more applied signal applicators in communication with the applied signal generator for applying one or more of the applied signals to each test zone each applied signal applicator being attachable to one of the test zones and having a capability for automated, continuous application, for a selected signal application time interval, of the one or more applied signals generated by the applied signal generator;
   one or more applied signal resistance sensors for measuring the resistance of the skin of the subject at each of the test zones as a function of time, as applied signals are applied to the test zones, each applied signal resistance sensor being attachable to one of the test zones and having a capability for automated, continuous measurement of resistance for a selected resistance measurement time interval;

resistance memory in communication with the applied signal resistance sensors; and an actuator in communication with the resistance memory, the actuator having a capability for the determination of resistance as a function of time, the resistance time function.

24. Apparatus as recited in claim 23 wherein the applied signal selector further comprises an applied signal memory and an applied signal library stored on the applied signal memory.

25. Apparatus as recited in claim 23 wherein the applied signal selector further comprises an applied signal memory and an applied signal library stored on the applied signal memory.

26. Apparatus as recited in claim 23 wherein one or more of the applied signal applicators is an electrical contact connection or pad.

27. Apparatus as recited in claim 23 wherein one or more of the applied signal applicators is an electrical contact finger connection or pad.

28. Apparatus as recited in claim 27 wherein each of the electrical contact finger connections or pads has a finger band for fixedly positioning the electrical contact finger connection or pad against a desired test zone on a selected finger of the human subject.

29. Apparatus as recited in claim 23 wherein each signal resistance sensor is an ohmmeter.

30. Apparatus as recited in claim 23 wherein the voltage characteristics of the applied signal is known and wherein each signal resistance sensor is a current meter which measures the current flowing from a respective applied signal applicator to a respective test zone.

31. Apparatus as recited in claim 23 wherein a maximum resistance measured during a selected time interval is determined from the resistance time function.

32. Apparatus as recited in claim 31 wherein a minimum resistance measured following the maximum resistance during the selected time interval is determined from the resistance time function.

33. Apparatus as recited in claim 32 wherein a resistance fall rate, which is the resistance decrease between the maximum resistance and the minimum resistance, divided by an elapsed fall time between the time of the maximum resistance and the time of the minimum resistance is determined from the resistance time function.

34. Apparatus as recited in claim 31 wherein a resistance rise rate which is the maximum resistance divided by an elapsed rise time between the time of the maximum resistance and the time the applied signal is applied to the respective test zone is determined from the resistance time function.

35. Apparatus as recited in claim 23 wherein a resistance vector is determined from the resistance time function.

36. Apparatus as recited in claim 23 wherein a slope of the resistance time function as a function of time is determined from the resistance time function.

37. Apparatus as recited in claim 23 wherein a resistance vector having a maximum resistance measured during a selected time interval as one vector component and an elapsed rise time between the time of the maximum resistance and the time the applied signal is applied to the respective test zone as another vector component is determined from the resistance time function.

38. Apparatus as recited in claim 23 wherein the actuator is in communication with the applied signal selector, the applied signal generator, the applied signal applicator, and the applied signal resistance sensors.

39. Apparatus as recited in claim 23 wherein the actuator is a digital computer.

40. Apparatus as recited in claim 23 further comprising a digital computer actuator, the actuator having applied signal memory and an applied signal library stored on the applied signal memory.

41. Apparatus as recited in claim 23 further comprising a digital computer actuator, the actuator having resistance memory in communication with the applied signal resistance sensors.

42. Apparatus as recited in claim 23 wherein the applied signal is a base signal comprising a constant voltage square wave signal applied for a base signal time period.

43. Apparatus as recited in claim 23 wherein the applied signal is a stimulus signal comprising a variable square wave signal applied for a stimulus signal time period.

44. Apparatus as recited in claim 23 wherein the applied signal is a composite signal comprising a base signal which comprises a constant voltage square wave signal applied for a base signal time period and a stimulus signal which comprises a variable square wave signal applied for a stimulus signal time period.

45. Method for the automated measurement of a resistance time function which is resistance as a function of time for a selected time interval for one or more test zones on the skin of a human subject, the method comprising:
   a) selecting one or more applied signal forms;
   b) generating a respective applied signal for each selected applied signal form, each applied signal being an electric voltage signal determined by the form of the applied signal form for which it is generated;
   c) applying, with one or more applied signal applicators, one or more of the applied signals to each test zone, each applied signal applicator being attachable to one of the test zones and having a capability for automated, continuous application, for a selected signal application time interval, of the one or more applied signals generated by the applied signal generator;
   d) measuring, with one or more applied signal resistance sensors, the resistance of the skin of the subject at each of the test zones as a function of time, as applied signals are applied to the test zones, each applied resistance sensor being attachable to one of the test zones and having a capability for automated, continuous measurement of resistance for a selected resistance measurement time interval;
   e) storing the resistance measurements in resistance memory in communication with the applied signal resistance sensors; and
   f) determining resistance as a function of time, the resistance time function.

* * * * *